(12) United States Patent
O'Lenick, Jr. et al.

(10) Patent No.: US 6,840,469 B1
(45) Date of Patent: Jan. 11, 2005

(54) PROCESS FOR COATING PARTICULATES WITH PHOSPHATED CASTOR OIL

(75) Inventors: Anthony J. O'Lenick, Jr., Dacula, GA (US); John Imperante, Somerville, NJ (US)

(73) Assignee: Phoenix Research Corporation, Somerville, NJ (US)

( * ) Notice: Subject to any disclaimer, the term of this patent is extended or adjusted under 35 U.S.C. 154(b) by 475 days.

(21) Appl. No.: 10/004,644

(22) Filed: Dec. 7, 2001

Related U.S. Application Data

(63) Continuation-in-part of application No. 09/854,090, filed on May 14, 2001, now Pat. No. 6,528,667.

(51) Int. Cl.[7] ................................................. B02C 19/12
(52) U.S. Cl. ............................ 241/21; 241/25; 366/348
(58) Field of Search ............................... 241/21, 25, 16, 241/22, 30; 366/348; 554/79; 558/164

(56) References Cited

U.S. PATENT DOCUMENTS

| 4,770,766 A | * | 9/1988 | Keller et al. .................... 209/5 |
| 5,786,389 A | | 7/1998 | O'Lenick |
| 6,528,667 B2 | | 3/2003 | O'Lenick et al. |

* cited by examiner

*Primary Examiner*—Mark Rosenbaum

(57) ABSTRACT

The present invention relates to phosphated derivatives of castor oil and hydrogenated castor oil as well as phosphated esters of ricinoleic acid. The inclusion of the phosphate group results in improved water solubility and a series of dispersants and emulsifiers that provide excellent particulate dispersing properties.

9 Claims, No Drawings

PROCESS FOR COATING PARTICULATES WITH PHOSPHATED CASTOR OIL

RELATED APPLICATIONS

This application is a continuation in part of Ser. No. 09/854,090 filed May 14, 2001, now U.S. Pat. No. 6,528,667 issued Mar. 4, 2003.

FIELD OF THE INVENTION

The present invention relates to a process for coating particulates with a phosphated derivative of castor oil or hydrogenated castor oil as well as phosphated esters of ricinoleic acid. The inclusion of the phosphate group results in improved water solubility and a series of dispersants and emulsifiers that provide excellent particulate dispersing properties. The word particulate is meant to include pigments and bismuth oxychloride, titanated mica, filmed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof The above mentioned powders may be surface treated with lecithin, amino acids, mineral oil silicone oil or various other agents either alone or in combination, which coat the powder surface and render the particles more lipophilic in nature. The word processing is meant to include milling, grinding, crushing or pulverizing. The oil is added to provide a vehicle into which the particulate is placed to facilitate the processing and provide a coating of the particulate.

BACKGROUND OF THE INVENTION

Castor oil is a unique triglyceride. It is derived from Ricinus communis L. The castor plant grows wild in many subtropical and tropical areas Today Brazil, China and India provide over 90% of the oil. Castor oil contains a large content of hydroxy containing compounds that are unsaturated.

Castor Oil is a clear, viscous, fight colored fluid that is nondrying and quite stable. The Purity of Castor Oil occurs with remarkable uniformity. Regardless of country of origin, or season it is grown, the composition and chemical properties remain within a very narrow range. Castor Oil has broad compatibility with oils, waxes, natural resins, and gums.

Another unique aspect of castor oil is the high level of ricinoleic acid in the molecule. Castor oil contains 89% of the acid, which conforms to the following structure;

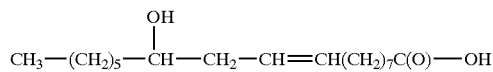

When hydrogenated the double bond is lost giving hydrogenated ricinoleic, or 12-hydroxy stearic acid.

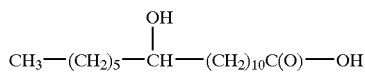

When the acids derived from castor (ricinoleic acid) are reacted with alcohols having 6 to 22 carbon atoms the resulting esters are also suitable candidates for phosphation.

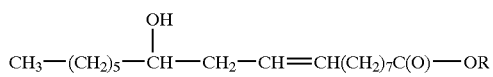

wherein R is $CH_3-(CH2)_n-$ and n is an integer ranging from 5 to 21.

When the acids derived from hydrogenated castor (12-hydroxy-stearic acid) are reacted with alcohols having 6 to 22 carbon atoms the resulting esters are also suitable candidates for phosphation.

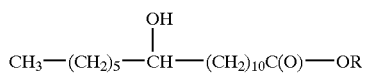

wherein R is $CH_3-(CH_2)_n-$ and n is an integer ranging from 5 to 21.

SUMMARY OF THE INVENTION

The present invention relates to use of a series of compounds in which the hydroxyl group in alkyl group of castor is phosphated, resulting in a surface-active agent that has outstanding particulate dispersing properties. Included within this definition of castor compounds are castor oil (a triglyceride), hydrogenated castor oil, ricinoleic acid and 12-hydroxystearic acid compounds. The present invention relates to a process for processing particulate with a phosphated derivative of castor oil or hydrogenated castor oil as well as phosphated esters of ricinoleic acid. The inclusion of the phosphate group results in improved water solubility and a series of dispersants and emulsifiers that provide excellent particulate dispersing properties. The word particulate is meant to include bismuth oxychloride, titanated mica, fumed silica, spherical silica, potymethyltnethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, ice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof The above mentioned powders may be surface treated with lecithin, amino acids, mineral oil, silicone oil or various other agents either alone or in combination, which coat the powder surface and render the particles more lipophilic in nature. The word processing is meant to include milling, grinding, crushing or pulverizing. The oil is added to provide a vehicle into which the particulate is placed to facilitate the processing and provide a coating of the particulate.

The invention also relates to the utilization of these phosphated materials as surface-active agents in personal care and industrial applications. These materials function as particulate wetters, and emulsifiers. As particulate wetters the compounds of the present invention coat the hydrophobic particulate making them disperse in aqueous formulations. The compounds of the present invention have the proper balance of water loving and oil loving portions to allow for the formation of very stable particulate dispersions.

OBJECTIVE OF THE INVENTION

It is the objective of the present invention to provide particulate wetting and dispersing agents derived from the phosphation of castor oil, hydrogenated castor oils or esters derived there from. The compounds are outstanding particulate dispersants. Additionally, the objective of the present invention is the utilization of the compounds of the present invention with particulates to make dispersions of outstanding stability.

DETAILED DESCRIPTION OF THE INVENTION

The present invention, is a process for dispersing particulate with a phosphated derivative of castor oil or hydrogenated castor oil as well as phosphated esters of ricinoleic acid. The inclusion of the phosphate group results in improved water solubility and a series of dispersants and emulsifiers that provide excellent particulate dispersing properties. The word particulate is meant to include pigments and bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone oil or various other agents either alone or in combination, which coat the powder surface and render the particles more lipophilic in nature. The word processing is meant to include milling, grinding, crushing or pulverizing. The oil is added to provide a vehicle into which the particulate is placed to facilitate the processing and provide a coating of the particulate castor oil is phosphated using poly phosphoric acid (PPA). The resulting product ranges from water dispersible, when only one of the three hydroxyl groups is phosphated, to water soluble when all three are phosphated.

The present invention is directed toward a process for dispersing particulates which comprises mixing a phosphated triglyceride conforming to the following structure

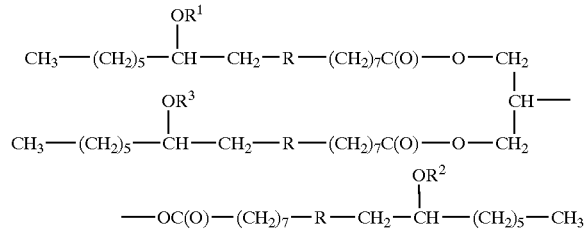

wherein;
R is selected from the group consisting of —(CH$_2$)$_2$— and —CH—CH—;

$R^1$ is —P(O)—(OH)$_2$
$R^2$ and $R^3$ are independently selected from the group consisting of H and —P(O)—(OH)2 with a particulate selected from the group consisting of bismuth oxychloride, titanium dioxide, zinc oxide, ferric oxide, ferric titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's ear, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica sibylate, silk powder, sericite, soy flour, tin oxide, titanium hydroxide, trimagnesium phosphate, walnut shell powder, or mixtures thereof and optionally milling, grinding, or homogenizing the mixture to obtain the desired particle size.

One subset set of the generic set compounds used in the process of the present invention conforms to the following structure based upon hydrogenated castor oil;

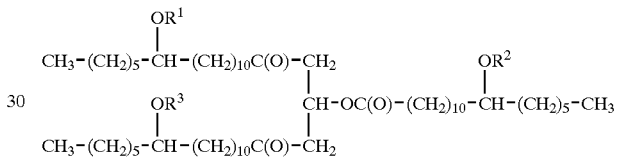

wherein;

$R^1$ is —P(O)—(OH)$_2$ $R^2$ and $R^3$ are independently selected from the group consisting of H and —P(O)—(OH)$_2$.

Another subset of compounds useful in the process of the present invention is based upon castor oil and conforms to the following structure;

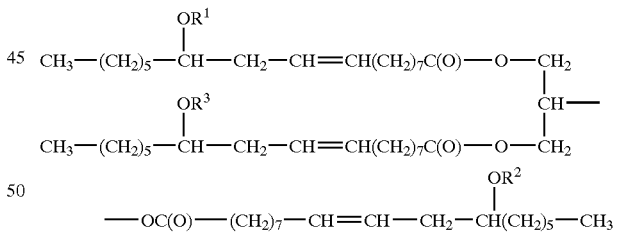

wherein;

$R^1$ is —P(O)—(OH)$_2$ $R^2$ and $R^3$ are independently selected from the group consisting of H and —P(O)—(OH)$_2$.

Another set of compounds useful in the process of the present invention confirm to the following structure;

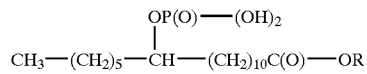

Finally, another set of compounds useful in the process of the present invention conforms to the following structure;

$$\text{CH}_3-(\text{CH}_2)_5-\underset{\underset{\text{OP(O)}-(\text{OH})_2}{|}}{\text{CH}}-\text{CH}_2-\text{CH}=\text{CH}(\text{CH}_2)_7\text{C(O)}-\text{OR}$$

wherein R is $\text{CH}_3-(\text{CH}_2)_n-$ and n is an integer ranging from 5 to 21.

The reaction with castor oil is as follows;

$$\text{CH}_3-(\text{CH}_2)_5-\underset{\underset{\text{OH}}{|}}{\text{CH}}-\text{CH}_2-\text{CH}=\text{CH}(\text{CH}_2)_7\text{C(O)}-\text{O}-\text{CH}_2$$
$$\text{CH}_3-(\text{CH}_2)_5-\underset{\underset{\text{OH}}{|}}{\text{CH}}-\text{CH}_2\text{CH}=\text{CH}(\text{CH}_2)_7\text{C(O)}-\text{O}-\text{CH}$$
$$-\text{OC(O)}-(\text{CH}_2)_7-\text{CH}=\text{CH}-\text{CH}_2-\underset{\underset{\text{OH}}{|}}{\text{CH}}(\text{CH}_2)_5-\text{CH}_3$$

+PPA $$\text{CH}_3-(\text{CH}_2)_5-\underset{\underset{\text{OP(O)}-(\text{OH})_2}{|}}{\text{CH}}-\text{CH}_2-\text{CH}=\text{CH}(\text{CH}_2)_7\text{C(O)}-\text{O}-\text{CH}_2$$
$$\text{CH}_3-(\text{CH}_2)_5-\underset{\underset{\text{OH}}{|}}{\text{CH}}-\text{CH}_2\text{CH}=\text{CH}(\text{CH}_2)_7\text{C(O)}-\text{O}-\text{CH}$$
$$-\text{OC(O)}-(\text{CH}_2)_7-\text{CH}=\text{CH}-\text{CH}_2-\underset{\underset{\text{OH}}{|}}{\text{CH}}(\text{CH}_2)_5-\text{CH}_3$$

The reaction for the hydrogenated castor is identical to that of the castor, except the double bond is not present. This results in a phosphated castor wax. The reaction proceeds as follows:

$$\text{CH}_3-(\text{CH}_2)_5-\underset{\underset{\text{OH}}{|}}{\text{CH}}-(\text{CH}_2)_{10}\text{C(O)}-\text{O}-\text{CH}_2$$
$$\text{CH}_3-(\text{CH}_2)_5-\underset{\underset{\text{OH}}{|}}{\text{CH}}-(\text{CH}_2)_{10}\text{C(O)}-\text{O}-\text{CH}$$
$$-\text{OC(O)}-(\text{CH}_2)_{10}-\underset{\underset{\text{OH}}{|}}{\text{CH}}-(\text{CH}_2)_5-\text{CH}_3$$

+PPA $$\text{CH}_3-(\text{CH}_2)_5-\underset{\underset{\text{OP(O)}-(\text{OH})_2}{|}}{\text{CH}}-(\text{CH}_2)_{10}\text{C(O)}-\text{O}-\text{CH}_2$$
$$\text{CH}_3-(\text{CH}_2)_5-\underset{\underset{\text{OH}}{|}}{\text{CH}}-(\text{CH}_2)_{10}\text{C(O)}-\text{O}-\text{CH}$$
$$-\text{OC(O)}-(\text{CH}_2)_{10}-\underset{\underset{\text{OH}}{|}}{\text{CH}}-(\text{CH}_2)_5-\text{CH}_3$$

The changing of the amount of PPA will allow for phosphating the remaining hydroxyl groups resulting in a di-phosphate (if 2 equivalents of PPA are used), or a Phosphated ricinoleic acid ester conform to the following structure $$\text{CH}_3-(\text{CH}_2)_5-\underset{\underset{\text{OR}^1}{|}}{\text{CH}}-\text{CH}_2-\text{CH}=\text{CH}(\text{CH}_2)_7\text{C(O)}-\text{O}-\text{R}$$

wherein;

R is $-(\text{CH}_2)\text{n}-\text{CH}_3$ $R^1$ is $-\text{P(O)}-(\text{OH})_2$ n is an integer ranging from 5 to 21.

Phosphated 12-hydroxy stearic acid esters conform to the following structure $$\text{CH}_3-(\text{CH}_2)_5-\underset{\underset{\text{OR}^1}{|}}{\text{CH}}(\text{CH}_2)_{10}\text{C(O)}-\text{O}-\text{R}$$

wherein;

R is $-\text{CH}_2)\text{n}-\text{CH}_3$ $R^1$ is $-\text{P(O)}-(\text{OH})_2$ n is an integer ranging from 5 to 21

Preferred Embodiments

In a preferred embodiment the phosphated compounds belong to class 1 and conforming to the following structure;

$$\text{CH}_3-(\text{CH}_2)_5-\underset{\underset{\text{OR}^1}{|}}{\text{CH}}-(\text{CH}_2)_{10}\text{C(O)}-\text{CH}_2$$
$$\text{CH}_3-(\text{CH}_2)_5-\underset{\underset{\text{OR}^3}{|}}{\text{CH}}-(\text{CH}_2)_{10}\text{C(O)}-\text{CH}_2$$
$$\underset{\underset{\text{OR}^2}{|}}{\text{CH}}-\text{OC(O)}-(\text{CH}_2)_{10}-\text{CH}-(\text{CH}_2)_5-\text{CH}_3$$

wherein;

$R^1$ is $-\text{P(O)}-(\text{OH})_2$ $R^2$ and $R^3$ are independently selected from the group consisting of H and $-\text{P(O)}-(\text{OH})_2$.

In a preferred embodiment of class 1 $R^2$ and $R^3$ are H.

In a preferred embodiment of class 1 $R^2$ is $-\text{P(O)}-(\text{OH})_2$ and $R^3$ is H.

In a preferred embodiment of class 1 $R^2$ and $R^3$ are both $-\text{P(O)}-(\text{OH})_2$ In a preferred embodiment of class 2 the phosphated compound conforming to the following structure $$\text{CH}_3-(\text{CH}_2)_5-\underset{\underset{\text{OR}^1}{|}}{\text{CH}}-\text{CH}_2-\text{CH}=\text{CH}(\text{CH}_2)_7\text{C(O)}-\text{O}-\text{CH}_2$$
$$\text{CH}_3-(\text{CH}_2)_5-\underset{\underset{\text{OR}^3}{|}}{\text{CH}}-\text{CH}_2-\text{CH}=\text{CH}(\text{CH}_2)_7\text{C(O)}-\text{O}-\text{CH}$$
$$-\text{OC(O)}-(\text{CH}_2)_7-\text{CH}=\text{CH}-\text{CH}_2-\underset{\underset{\text{OR}^2}{|}}{\text{CH}}(\text{CH}_2)_5-\text{CH}_3$$

wherein;

$R^1$ is $-\text{P(O)}-(\text{OH})_2$ $R^2$ and $R^3$ are independently selected from the group consisting of H and $-\text{P(O)}-(\text{OH})_2$.

In a preferred embodiment of class 2 $R^2$ and $R^3$ are H.

In a preferred embodiment of class 2 $R^2$ is $-\text{P(O)}-(\text{OH})_2$ and $R^3$ is H.

In a preferred embodiment of class 2 $R^2$ and $R^3$ are both $-\text{P(O)}-(\text{OH})_2$ In a preferred embodiment of class 3 the phosphated compound conforming to the following structure;

$$\text{CH}_3-(\text{CH}_2)_5-\underset{\underset{\text{OR}^1}{|}}{\text{CH}}(\text{CH}_2)_{10}\text{C(O)}-\text{O}-\text{R}$$

wherein;

R is —CH$_2$)n—CH$_3$

R$^1$ is —P(O)—(OH)$_2$ n is an integer ranging from 5 to 21.

In a preferred embodiment of class 3 n is 5.

In a preferred embodiment of class 3 n is 11.

In a preferred embodiment of class 3 n is 17.

In a preferred embodiment of class 3 n is 21.

In a preferred embodiment of class 4 the phosphated compound conforming to the following structure

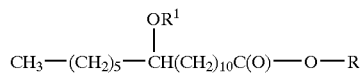

wherein;

R is —(CH$_2$)n—CH$_3$,

Ris —P(O)—(OH)$_2$, n is an integer ranging from 5 to 21.

In a preferred embodiment of class 3 n is 5.

In a preferred embodiment of class 3 n is 11.

In a preferred embodiment of class 3 n is 17.

In a preferred embodiment of class 3 n is 21.

Examples

Castor oil is an item of commerce and is commercially available from a variety of sources including the Fanning Corporation of Chicago Ill.

Polyphosphoric Acid is an item of commerce and is sometimes called 115% phosphoric acid.

Ricinoleic esters are items of commerce and are commercially available from Phoenix Chemical Somerville, N.J. They conform to the following structure:

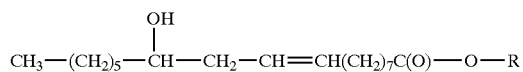

wherein;

R is —CH$_2$)n—CH$_3$ n is an integer ranging from 5 to 21

| Example | n |
|---|---|
| Raw Material 1 | 5 |
| Raw Material 2 | 11 |
| Raw Material 3 | 17 |
| Raw Material 4 | 21 |

12-hydroxy stearic acid esters are items of commerce and are commercially available from Phoenix Chemical, Somerville, N.J. They conform to the following structure:

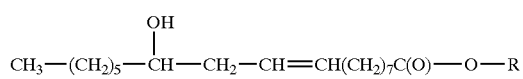

R is —CH$_2$)n—CH$_3$ n is an integer ranging from 5 to 21.

| Example | n |
|---|---|
| Raw Material 5 | 5 |
| Raw Material 6 | 11 |
| Raw Material 7 | 17 |
| Raw Material 8 | 21 |

Phosphating Agents

Polyphosphoric Acid (PPA) is 115% phosphoric acid. The phosphates of this invention can be prepared by reacting the hydroxyl containing with a suitable Polyphosphoric acid. It will be understood that the product of phosphation, is a mixture of mono and di-ester.

The following examples further illustrate the objects and advantages of this invention, though it should be understood that the various reactants and amounts thereof, reaction conditions, and other details are merely illustrative and should not be construed to unduly limit this invention.

General Procedure

The specified amount of castor derivative is added to a suitable reaction vessel. The specified amount of potyphosphoric acid is charged to under good agitation over a 2 hr. period, under good agitation. The exothermic reaction raises the temperature of the mixture to about 70 C. After 1 hour slowly wise the temperature to 100 C an d hold 2–4 hours.

EXAMPLE 1

Castor Oil Product

Only One Hydroxyl Group on the Triglyceride Phosphated 939.0 grams of castor oil is added to a suitable reaction vessel. The 114 grams of Polyphosphoric acid is charged to under good agitation over a 2 hr. period, under good agitation. The exothermic reaction raises the temperature of the mixture to about 70 C. After 1 hour slowly raise the temperature to 100 C. and hold 2–4 hours.

EXAMPLE 2

Castor Oil Product

Two of the Three Hydroxyl Groups on the Triglyceride Phosphated 626.6 grams of castor oil is added to a suitable reaction vessel. The 114 grams of Polyphosphoric acid is charged to under good agitation over a 2 hr. period, under good agitation. The exothermic reaction raises the temperature of the mixture to about 70 C. After 1 hour slowly raise the temperature to 100 C. and hold 2–4 hours.

EXAMPLE 3

Castor Oil Product

All Three Hydroxyl Groups on the Triglyceride Phosphated 313.3 grams of castor oil is added to a suitable reaction vessel. The 114 grams of Polyphosphoic acid is charged to under good agitation over a 2 hr. period under good agitation. The exothermic reaction raises the temperature of the mixture to about 70 C. After 1 hour slowly raise the temperature to 100 C. and hold 2–4 hours.

EXAMPLE 4

Hydrogenated Castor Oil Product

Only One Hydroxyl Group on the Triglyceride Phosphated 933.0 grams of hydrogenated castor oil is added to a suitable reaction vessel. The 114 grams of Polyphosphoric aid is charged to under good agitation over a 2 hr. period, under good agitation. The exothermic reaction raises the temperature of the mixture to about 70 C. After 1 hour slowly raise the temperature to 100 C. and hold 2–4 hours.

EXAMPLE 5

Hydrogenated Castor Oil Product

Two of the Three Hydroxyl Groups on the Triglyceride Phosphated 6220 grams of hydrogenated castor oil is added to a suitable reaction vessel. The 114 grams of Polyphosphoric acid is charged to under good agitation over a 2 hr. period, under good agitation. The exothermic reaction raises the temperature of the mixture to about 70 C. After 1 hour slowly raise the temperature to 100 C. and hold 2–4 hours.

EXAMPLE 6

Hydrogenated Castor Oil Product

All Three Hydroxyl Groups on the Triglyceride Phosphated 311.0 grams of hydrogenated castor oil is added to a suitable reaction vessel. The 114 grams of Polyphosphoic acid is charged to under good agitation over a 2 hr. period, under good agitation. The exothermic reaction raises the temperature of the mixture to about 70 C. After 1 hour slowly raise the temperature to 100 C. and hold 2–hours.

EXAMPLE 7

522,5 grams of castor oil is added to a stable reaction vessel, The 114 grams of Polyphosphoric acid is charged to under good agitation Over a 2 hr. period, under good agitation. The exothermic reaction raises the temperature of the mixture to about 70 C. After 1 hour slowly raise the temperature to 100 C. and hold 2–4 hours.

EXAMPLE 8

Ricinoleic Esters 800.0 grams of ricinoleic ester Raw Material Example 1 is added to a suitable reaction vessel. The 114 grams of Polyphosphoric acid is charged to under good agitation over a 2 hr. period, under good agitation. The exothermic reaction raises the temperature of the mixture to about 70 C. After 1 hour slowly raise the temperature to 100 C and hold 2–4 hours.

EXAMPLE 9

972.0 grams of ricinoleic ester Raw Material Example 2 is added to a suitable reaction vessel. The 114 grams of Polyphosphoric acid is charged to under good agitation over a 2 hr. period, under good agitation. The exothermic reaction raises the temperature of the mixture to about 70 C. After 1 hour slowly raise the temperature to 100 C. and hold 2–4 hours.

EXAMPLE 10

1320.0 grams of ricinoleic ester Raw Material Example 3 is added to a suitable reaction vessel. The 114 grams of Polyphosphoric acid is charged to under good agitation over a 2 hr. period, under good agitation. The exothermic reaction raises the temperature of the mixture to about 70 C. After 1 hour slowly raise the temperature to 100 C. and hold 2–4 hours.

EXAMPLE 11

Ricinoleic Ester 1600.0 grams of ricinoleic ester Raw Material Example 4 is added to a suitable reaction vessel. The 114 grams of Polyphosphoric acid is charged to under good agitation over a 2 hr. period, under good agitation. The exothermic reaction raises the temperature of the mixture to about 70 C. After 1 hour slowly raise the temperature to 100 C. and hold 2–4 hours.

EXAMPLE 12

12-hydroxy-stearic ester 802.0 grams of 12-hydroxy stearic ester Raw Material Example 5 is added to a suitable reaction vessel. The 114 grams of Polyphosphoric acid is charged to under good agitation over a 2 hr. period, under good agitation, The exothermic reaction raises the temperature of the mixture to about 70 C. After 1 hour slowly raise the temperature to 100 C. and hold 2–4 hours.

EXAMPLE 13

12-hydroxy-stearic ester 1010.0 grams of 12-hydroxy stearic ester Raw Material Example 6 is added to a suitable reaction vessel. The 114 grams of Polyphosphoric acid is charged to under good agitation over a 2 hr. period, under good agitation. The exothermic reaction raises the temperature of the mixture to about 70 C. After 1 hour slowly raise the temperature to 100 C. and hold 2–4 hours.

EXAMPLE 14

12-hydroxy-stearic ester 1410.0 grams of 12-hydroxy stearic ester Raw Material Example 7 is added to a suitable reaction vessel. The 114 grams of Polyphosphoric acid is charged to under good agitation over a 2 hr. period, under good agitation. The exothermic reaction raises the temperature of the mixture to about 70 C. After 1 hour slowly raise the temperature to 100 C. and hold 2–4 hours.

EXAMPLE 15

12-hydroxy-stearic ester 666.6 grams of 12-hydroxy stearic ester Raw Material Example 8 is added to a suitable reaction vessel. The 114 grams of Polyphosphoric acid is charged to under good agitation over a 2 hr. period, under good agitation. The exothermic reaction raises the temperature of the mixture to about 70 C. After 1 hour slowly raise the temperature to 100 C. and hold 2–4 hours.

Applications Examples

The compounds of the present invention examples 1–15 are water dispersible to varying extents depending upon the percentage of phosphate in the molecule. The lower the amount of phosphate in the molecule the more castor oil soluble the product. The higher the amount of the phosphate present the more water-soluble the product. The compounds make very efficient emulsifiers. Low percentage phosphate products favor water in oil emulsions, the higher the level of phosphate favor oil in water emulsions.

The compounds of the present invention are also very efficient particulate dispersants. The particulates used in color cosmetics are ground into low particle size in an oil phase. The phosphated products of the present invention allow for effective grinding and promote coatings that allow for easy dispersion in emulsions for use in personal care products.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patent able novelty which reside in the present invention, including all features which would be treated as equivalents thereof by those skilled in the art to which the invention pertains.

We claim:

1. A process for dispersing particulate, which comprise mixing an effective dispersing amount of a phosphated triglyceride conforming to the following structure

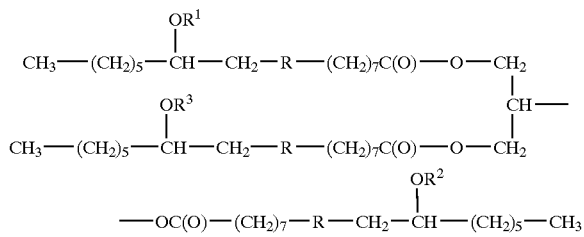

wherein;
R is selected form the group consisting of —(CH$_2$)$_2$— and —CH—CH—;
R$^1$ is —P(O)—(OH)$_2$;
R$^2$ and R$^3$ a independently select from the group consisting of H and —P(O)—(OH)$_2$
with a particulate selected from the group consisting of bismuth oxychloride, titanium dioxide, zinc oxide, ferric oxide, ferric titanated mica, fumed silica, spherical silica, polymethylmethacrylate, micronized teflon, boron nitride, acrylate copolymers, aluminum silicate, aluminum star octenylsuccinate, bentonite, calcium silicate, cellulose, chalk, corn starch, diatomaceous earth fuller's earth glyceryl starch hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof and optionally milling, grinding, or homogenizing the mixture.

2. A process of claim 1 wherein the effective dispersing concentration of phosphated triglyceride ranges from 1 to 50% by weight.

3. A process of claim 2 wherein R$^2$ and R$^3$ are H.

4. A process of claim 2 wherein R$^2$ is —P(O)—(OH)$_2$ and R$^3$ is H.

5. A process of claim 1 wherein R is —CH═CH—.

6. A process of claim 5 wherein R$^2$ and R$^3$ and both —P(O)—(OH)$_2$.

7. A process of claim 1 wherein R is —(CH$_2$)$_2$—.

8. A process of claim 7 wherein R$^2$ and R$^3$ are H.

9. A process for dispersing particulate which comprises mixing an effective dispersing amount of a phosphated ester selected from the group consisting of

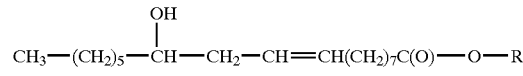

wherein R is CH$_3$—(CH$_2$)$_n$— and n is an integer ranging from 5 to 21; and

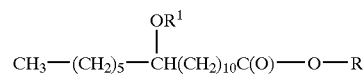

wherein;
R is —(CH$_2$)n—CH$_3$
R$^1$ is —P(O)—(OH)$_2$
n is an integer ranging from 5 to 21;
with a particulate selected from the group consisting of bismuth oxychloride, titanium dioxide, zinc oxide, ferric oxide, ferric titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof and optionally milling, grinding, or homogenizing the mixture.

* * * * *